United States Patent

Ratajczak et al.

Patent Number: 5,312,009
Date of Patent: May 17, 1994

[54] LIQUID SPECIMEN COLLECTOR WITH REMOVABLE EXTRACTION DEVICE

[75] Inventors: Janet Ratajczak, McHenry; Lawrence G. Ponsi, Wheeling; Paul H. Hanifl, Barrington Hills, all of Ill.

[73] Assignee: Sage Products, Inc., Crystal Lake, Ill.

[21] Appl. No.: 73,098

[22] Filed: Jun. 7, 1993

[51] Int. Cl.$^5$ .................................. B65D 55/08
[52] U.S. Cl. ................... 220/258; 222/542; 206/229; 206/222
[58] Field of Search ............... 220/254, 258; 206/229, 206/222, 219; 222/542, 402.1, 402.21, 402

[56] References Cited

U.S. PATENT DOCUMENTS

| | | | |
|---|---|---|---|
| 2,639,806 | 5/1983 | Recht | 206/229 |
| 3,433,712 | 3/1969 | Gerarde | 206/229 |
| 3,579,306 | 5/1971 | Crane | 206/229 |
| 3,655,096 | 4/1972 | Easter | 206/229 |
| 3,698,868 | 10/1972 | Bilichniansky | 206/229 |
| 4,513,889 | 4/1985 | Beard | 220/258 |
| 5,145,083 | 9/1992 | Takahashi | 220/258 |
| 5,158,192 | 10/1982 | Lataix | 220/258 |

Primary Examiner—Joseph Man-Fu Moy
Attorney, Agent, or Firm—Lee, Mann, Smith, McWilliams, Sweeney, & Ohlson

[57] ABSTRACT

A liquid specimen collector for biological fluids. A receptacle is provided for holding fluids, with a cover applied thereon. A sample port is formed in the cover, and a cap is threadedly applied to the port. A removable specimen extractor is installed in the sample port, having a needle for piercing a pierceable end of a specimen vial, and an extraction tube which extends into the receptacle to facilitate withdrawal of any fluid in the receptacle. While the specimen extractor is removable, it is held temporarily in place until its removal is desired.

18 Claims, 2 Drawing Sheets

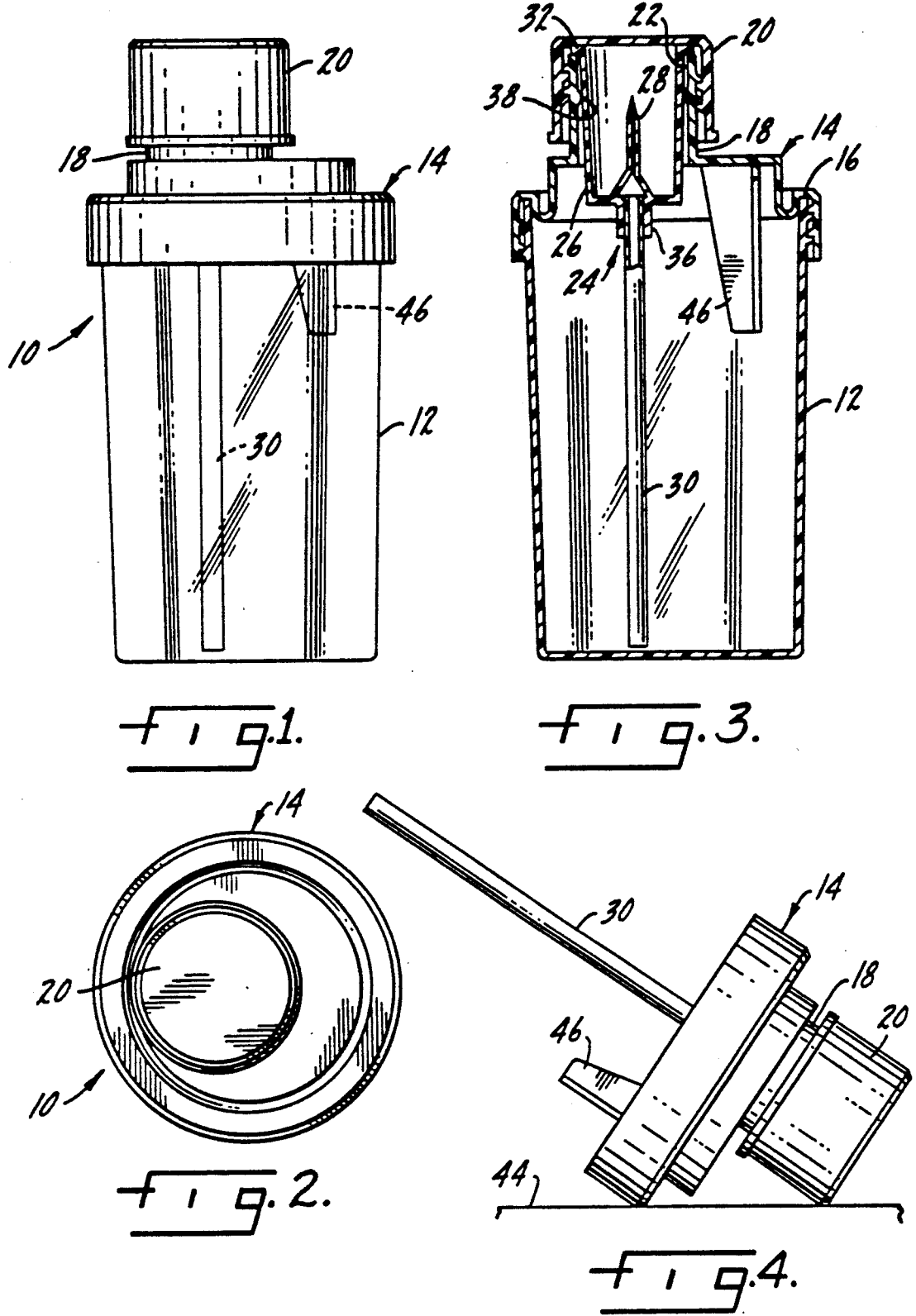

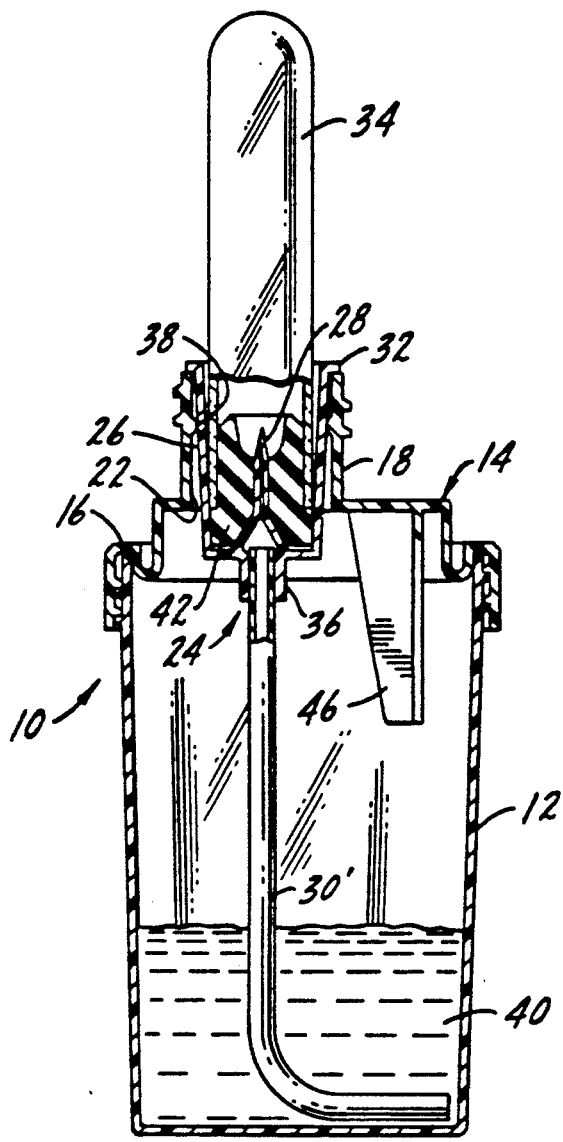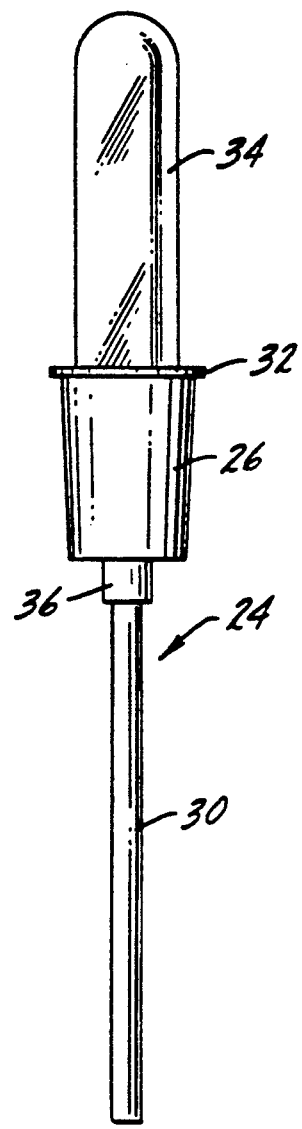

LIQUID SPECIMEN COLLECTOR WITH REMOVABLE EXTRACTION DEVICE

BACKGROUND OF THE INVENTION

This invention relates to sampling of biological fluids, such as urine, and particularly to a container for collection of such fluids and extraction of one or more samples therefrom.

Specimen collectors for biological fluids, in their simplest form, comprise simply a container with a removable cover. Once a sample has been collected in the container and the cover reapplied, the specimen collector is then transported to a laboratory, where sampling of the specimen takes place.

For more immediate sampling of the collected biological fluids, the collector can include additional features. For example, U.S. Pat. No. 4,300,404 describes a liquid specimen container which has not only a receptacle for fluids, but also an integral sampling portion comprising a recess with a needle extending upwardly therein. The needle is connected to a tube which extends into the container for withdrawing fluid therefrom. When the pierceable end of an air-evacuated vial is inserted in the recess and is pierced by the needle, a sample is withdrawn from the container without the need of removing the cover. Once the sample has been withdrawn, the sample collector can then be discarded, another sample withdrawn in the same manner, or the sample collector can be transported to a laboratory for further testing of the fluid therein.

Once a sample has been withdrawn from the specimen container of Pat. No. 4,300,404, the needle is contaminated, yet it remains with the specimen container since it is an integral part thereof. The only protection from the needle is a replaceable label which must be physically reapplied to the container after the sample or samples have been withdrawn. Not only is reapplication of a label cumbersome, it also exposes the doctor, nurse, lab technician or other person handling the container to possible infection.

SUMMARY OF THE INVENTION

The invention is directed to an improved container for collection of biological fluids. The container includes a receptacle for fluids, the receptacle having an open end to which a cover is applied to sealingly close the open end. A sample port is formed in the cover, and a cap is shaped to sealingly close the sample port. A removable specimen extractor is formed to be seated within the sample port. The specimen extractor includes a sample cup which is shaped to receive a pierceable end of a specimen vial. A hollow, upstanding needle is located within the cup and is positioned to pierce the pierceable end of the vial when the vial is received in the cup. An extraction tube extends from the cup in communication with the needle, the extraction tube, when the extractor is seated within the sample port, extending into the receptacle to facilitate withdrawal of fluid therefrom.

In accordance with the preferred form of the invention, the sample port is formed in an upstanding collar in the cover. The collar preferably is offset toward one edge of the cover, and a counterbalance is provided to counterbalance the cover such that, when the cover is removed from the receptacle and placed on a horizontal surface, the tube is inclined upwardly away from contact with the horizontal surface. In the preferred form of the invention, the counterbalance comprises a weight secured to the underside of the cover. The weight is offset toward the edge of the cover in an opposite direction to that which the collar is offset.

The invention includes means for temporarily retaining the specimen extractor in the sample port. The temporary retaining means comprises at least one protrusion in a downwardly depending wall of the sample port. Preferably the wall is cylindrical, and the protrusion or protrusions are annular protrusions extending from the wall.

To assure proper removal of liquid specimens from the receptacle, the extraction tube is at least as long as the depth of the receptacle. In accordance with one form of the invention, the tube is longer than the depth and therefore a portion of the tube adjoins the bottom of the receptacle.

BRIEF DESCRIPTION OF THE DRAWINGS

The invention is described in greater detail in the following description of examples embodying the best mode of the invention, taken in conjunction with the drawing figures, in which:

FIG. 1 is an elevational illustration of one form of a container according to the invention, FIG. 2 is a top plan view thereof, FIG. 3 is a cross-sectional view of the container shown in FIG. 1, illustrating detail, FIG. 4 is an elevational view of the cover for the container when removed from the container, and showing how the counterbalanced cover seeks a rest position with the extraction tube always extending at an upward angle, FIG. 5 is cross-sectional view similar to FIG. 3, but with the cap for the sample port removed and with a sampling vial being shown in place, and also illustrating an extended version of the extraction tube, and FIG. 6 is an elevational view of the sampling vial and specimen extractor when removed as a unit from the container.

DESCRIPTION OF EXAMPLES Embodying The Best Mode of the Invention

A container according to the invention is shown generally at 10 in the drawing figures. The container includes two basic portions, a receptacle 12 for holding fluids, and a cover 14 formed to be sealingly applied to an open end 16 of the container 12. The cover 14 and the receptacle 12 can include mating threads or any other means of temporarily applying the cover to the receptacle. A conventional fluid seal (not shown in detail) is also used.

The cover 14 includes an integral upstanding collar 18. As illustrated, preferably the collar 18 is offset toward one edge of the cover 14. A cap 20 is shaped to be sealingly applied to the collar 18. The cap 20 may include internal threads which engage similarly-formed threads in the upstanding collar 18. Other means of applying the cap 20 to the collar 18 may alternatively be employed, so long as the cap 20 is readily removable from the collar 18. A conventional fluid seal (not shown in detail) is also used.

The collar 18 includes an internal sample port 22, comprising a downwardly depending cylindrical wall in the collar 18. A removable specimen extractor 24 is installed in the sample port 22. The specimen extractor 24 comprises a sample cup 26, a hollow, upstanding needle 28 and an extraction tube 30.

The sample cup 26 is shaped to extend within the sample port 22. The sample cup has a peripheral top flange 32 which seats on top of the collar 22, as shown in FIGS. 3 and 5. The sample cup 26 is shaped to receive a pierceable end of a specimen vial 34, as shown in FIG. 5.

The needle 28 is preferably integrally formed at the bottom of the sample cup 28. Alternatively, the needle can comprise a separate element, such as a metal needle, which extends through the bottom of the sample cup 26. For example, a double-ended cannula could be installed in the bottom of the sample cup 26.

The extraction tube 30, which is hollow, is installed in direct communication with the hollow needle 28. The tube 30 can be affixed to the bottom of the sample cup 26 in any conventional manner, the tube 30 being depicted as being inserted and affixed within an annular flange 36 formed in the bottom of the sample cup 26.

As illustrated, it is preferred that the tube 30 extend at least to the bottom of the receptacle 12 when the cover 14 is applied thereon. As shown in FIG. 5, however, the tube may be extended, as shown at 30' and therefore a portion of the tube 30' lies along the bottom of the receptacle 12. In this form of the invention, of course, the length of the tube 30' is greater than the depth of the receptacle 12.

It is preferred that the specimen extractor 24 be temporarily retained or restrained in the sample port 22 until removal of the specimen extractor 24 is desired. To this end, at least one protrusion 38 is provided in the sample port 22, the protrusion 38 extending in an annular fashion in engagement with the sample cup 26. As shown, the sample cup 26 is tapered so that a snug fit occurs between the sample cup 26 and the protrusion 38 when the flange 32 engages the top of the collar 18. In this manner, the specimen extractor 24 is held in place until its removal is desired. More than one protrusion 28 may be formed in the sample port 22, and instead of being formed in an annular fashion, the protrusion or protrusions 38 may be bumps or only portions of an annular protrusion which engage the wall of the sample cup 26. Other means of holding the sample cup 26 in place may also be employed.

As shown in FIG. 5, the sample port 22 is used in combination with the specimen vial 34 to withdraw a portion of a sample 40 within the container 10. The vial 34 may be an evacuated glass vial having a pierceable end 42 formed of rubber or another suitable material which can be pierced by the needle 28. The needle 28 extends sufficiently upwardly in the sample cup 26 to cleanly pierce the end 42 to permit the vacuum in the vial 34 to withdraw a desired portion of the sample 40 from the receptacle 12 to within the vial 34.

Once the vial 34 has withdrawn its available portion of the sample 40, the vial 34 and the specimen extractor 24 can be withdrawn from the sample port 22 as a unit, as shown in FIG. 6. Alternatively, the specimen extractor 24 can be held in place, by means of the protrusions 38 or otherwise, and the filled vial 34 may then be withdrawn individually.

Normally, the container 10 is provided with a sterile interior. Therefore, it is advantageous when the cover 14 is withdrawn that the interior portions of the cover not contact any surface and become contaminated. As best shown in FIG. 4, when the cover 14 is removed as a unit including the specimen extractor 24, the combined weight of the collar 18, cap 20 and cup 26 causes the cover 14 to sit on a horizontal surface 44 in the orientation illustrated. To assure that orientation, the cover 14 also includes a counterbalancing weight 46 extending from the underside of the cover 14. The weight 46 is offset toward an edge of the cover 14 opposite to that which the collar 18 is offset. This geometry, in combination with the weight 46, assures that the removed cover assembly always rests in the orientation illustrated, with the extraction tube 30 being inclined upwardly away from contact with the horizontal surface 44.

The container 10 according to the invention is intended to be used in the first instance by a patient, and then by a doctor, nurse or laboratory technician in the second instance for sampling of the collected specimen. The patient uses the container 10 by removing the entire cover assembly 14 and then providing the sample 40. The cover 14 is then reapplied by the patient, and the container 10 is given to the test person. That person removes the cap 20 and inserts the evacuated specimen vial 34 into the cup 26 until the needle 28 pierces the pierceable end 42. The vacuum of the vial 34 then causes a portion of the sample 40 to be drawn up the tube 30 into the vial 34. The vial 34 and specimen extractor 24 can then be withdrawn as a unit as would normally occur, as shown in FIG. 6, or the vial 34 can be removed from the extractor 24 and a second, third, etc. vial applied on the needle 28 to withdraw additional portions of the sample 40. Once the final desired portion is withdrawn, the specimen extractor 24 is removed with a vial 34, the cap 20 reapplied, and the container 10 is then discarded or further handled as desired.

It is preferred that all portions of the container 10 be formed of plastic for economy and ease of forming the parts and the seals. However, other materials can be employed, as desired.

Various changes can be made to the invention without departing from the spirit thereof or scope of the following claims.

What is claimed is:

1. A container for collection of biological fluids, comprising
   a. a receptacle for fluids, said receptacle having an open end,
   b. a cover formed to sealingly close said open end,
   c. a sample port formed in said cover,
   d. a cap shaped to sealingly close said sample port,
   e. a removable specimen extractor formed to be seated within said sample port, said specimen extractor including
      i. a sample cup shaped to receive a pierceable end of a specimen vial,
      ii. a hollow, upstanding needle located within said cup and positioned to pierce said pierceable end when said specimen vial is received in said cup, and
      iii. an extraction tube extending from said cup and communicating with said needle, said tube, when said extractor is seated with said sample port, extending into said receptacle to facilitate withdrawal of fluid therefrom.

2. A container according to claim 1 in which said cover includes an upstanding collar, said sample port being formed in said collar.

3. A container according to claim 2 in which said collar is offset toward one edge of said cover.

4. A container according to claim 3 in which said cover includes an upper side and an underside, said collar extending from said upper side, and including means counterbalancing said cover, when removed from said receptacle and placed on a surface, such that said tube is inclined upwardly away from contact wit the surface.

5. A container according to claim 4 in which said counterbalancing means comprises a weight secured to said underside.

6. A container according to claim 5 in which said weight is offset toward an edge of said cover opposite to said one edge.

7. A container according to claim 1 including means for temporarily retaining said specimen extractor in said sample port.

8. A container according to claim 7 in which said sample port includes a depending wall, and in which said means for temporarily retaining comprises at least one protrusion in said wall engaging said sample cup.

9. A container according to claim 8 in which said wall is cylindrical and said protrusion is annular.

10. A container according to claim 1 in which said receptacle has a predetermined depth and said extraction tube has a length greater than said depth such that a portion of said tube adjoins the bottom of said receptacle.

11. A container according to claim 1 in which said cover includes an upper side and an underside, and including means counterbalancing said cover, when removed from said receptacle and placed on a surface, such that said tube is inclined upwardly away from contact with the surface.

12. A container according to claim 11 in which said counterbalancing means comprises a weight secured to said underside.

13. A container according to claim 12 in which said weight is offset toward an edge of said cover.

14. A container for collection of biological fluids, comprising
 a. a cylindrical receptacle for fluids, said receptacle having an open end,
 b. a cover formed to sealingly close said open end,
 c. an upstanding sample port formed in said cover, said sample port being offset toward one edge of said cover,
 d. a cap shaped to sealingly close said sample port,
 e. a removable specimen extractor formed to be seated within said sample port, said specimen extractor including
  i. a sample cup shaped to receive a pierceable end of a specimen vial,
  ii. a hollow, upstanding needle located within said cup and positioned to pierce said pierceable end when said specimen vial is received in said cup, and
  iii. an extraction tube extending from said cup and communicating with said needle, said tube, when said extractor is seated with said sample port, extending into said receptacle to facilitate withdrawal of fluid therefrom, and
 f. means counterbalancing said cover, when removed from said receptacle and placed on a surface, such that said tube is inclined upwardly away from contact with the surface.

15. A container according to claim 14 in which said counterbalancing means comprises a weight secured to an underside of said cover.

16. A container according to claim 15 in which said weight is offset toward an edge of said cover opposite to said one edge.

17. A container according to claim 14 including means for temporarily retaining said specimen extractor in said sample port.

18. A container according to claim 17 in which said sample port includes a depending wall, and in which said means for temporarily retaining comprises at least one protrusion in said wall engaging said sample cup.

* * * * *